United States Patent

Kim et al.

[11] Patent Number: 5,817,808
[45] Date of Patent: Oct. 6, 1998

[54] PROCESS FOR PREPARING BENZODIAZEPINE DERIVATIVES

[75] Inventors: Yong Hae Kim; Jin Kyu Park, both of Seoul; Kwon Kim, Kyunggi-Do; Hee Sock Park, Taejeon, all of Rep. of Korea

[73] Assignee: Dong Kook Pharmaceutical Company, Inc., Seoul, Rep. of Korea

[21] Appl. No.: 925,273

[22] Filed: Sep. 8, 1997

[51] Int. Cl.[6] .................... C07D 498/04; C07D 487/00
[52] U.S. Cl. .......................... 540/498; 540/548
[58] Field of Search .................... 540/498, 548

[56] References Cited

U.S. PATENT DOCUMENTS

| | | | |
|---|---|---|---|
| 4,118,386 | 10/1978 | Walser | 260/239.3 |
| 4,316,839 | 2/1982 | Gerecke et al. | 260/239.3 |
| 4,870,073 | 9/1989 | Watjen et al. | 514/214 |
| 4,977,258 | 12/1990 | Houghton et al. | 540/548 |

OTHER PUBLICATIONS

Fryer et al., *J. Org. Chem.*, (1991) 56:11, pp. 3715–3719.
Kukla et al., *J. Med. Chem.*, (1991) 34:2, pp. 746–751.
Gu et al., *J. Med. Chem.*, (1993) 36:8, pp. 1001–1006.

*Primary Examiner*—Mukund J. Shah
*Assistant Examiner*—Bruck Kifle
*Attorney, Agent, or Firm*—Kenyon & Kenyon

[57] ABSTRACT

The object of the present invention is to provide an improved process for preparing benzodiazepine-3-alkyl carboxylate of formula(I) and its pharmaceutically acceptable salts and esters.

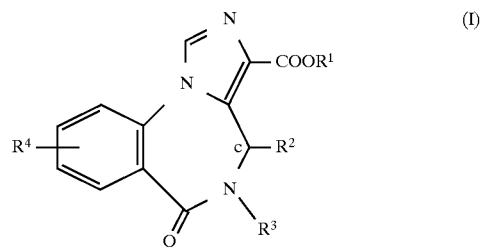

wherein $R^1$ is methyl, ethyl or isopropyl;

$R^2$ and $R^3$ are each independently hydrogen or $C_1$–$C_6$ lower alkyl;

$R^4$ is hydrogen, halogen or trifluoromethyl;

carbon atom denoted as c has the S— or R, S— configuration.

7 Claims, No Drawings

PROCESS FOR PREPARING BENZODIAZEPINE DERIVATIVES

(BACKGROUND OF THE INVENTION)

1. Field of the Invention

This invention relates to a novel process for preparing benzodiazepine-3-alkyl carboxylate derivatives, more specifically, a process for preparing [5,6-dihydro-5-methyl-6-oxo-4H-imidazo[1,5-a][1,4] benzodiazepine-3-alkyl carboxylate] derivatives from 2-amino benzoate derivatives as starting materials.

2. Description of Prior Art 8-fluoro-5,6-dihydro-5-methyl-6-oxo-4H-imidazo [1,5-a] [1,4] benzodiazepine-3-ethyl carboxylate (hereinafter refer to as flumazenil) was first synthesized and patented under U.S. Pat. No. 4,316,839 by Gerecke et al. in 1982. Flumazenil and its pharmaceutically acceptable salts and esters are now under study as an antagonist against 1,4-benzodiazepine tranquilizer having central-depressant, muscle relaxant, ataxic and respiratory depressant properties. Currently, flumazenil has been marketed as useful antagonist against benzodiazepine tranquilizer under tradename "Anexate" by Hoffman-La Roche Inc. Various kinds of methods for preparing benzodiazepine-3-alkyl carboxylate derivatives including flumazenil was disclosed by U.S. Pat. Nos. 4,118,386 and 4,316,839 and Belgium Pat. Nos. 833,248 and 839,364.

In U.S. Pat. No. 4,316,839, a fundamental process for synthesis of imidazo [1,5-1 ] [1,4] diazepine derivatives of following formula(2) was disclosed. In this process, the crucial step is cyclization reaction between alkyl isocyanate and i) imino phosphate or ii) imino halide as active form of amide radical. However, this preparation method has some difficulties for application owing to its low yield of end product.

The followings are reaction schemes of this method.

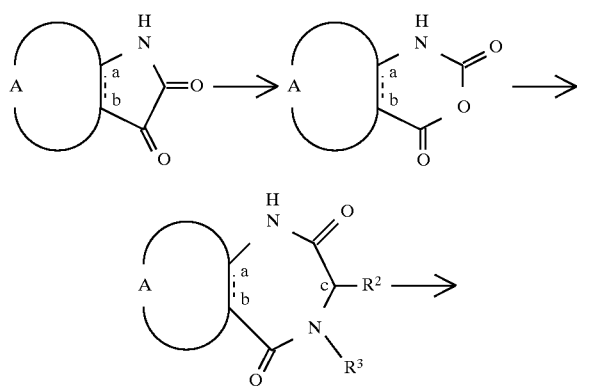

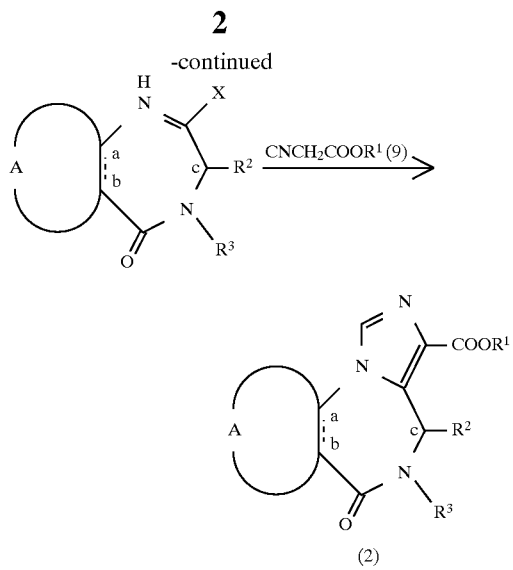

wherein
A together with the two carbon atoms denoted as a and b is selected from the group consisting of:

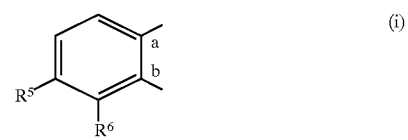

and

the dotted line represents the double bond;
$R^1$ is methyl, ethyl or isopropyl;
$R^2$ is hydrogen and $R^3$ is lower alkyl or
$R^2$ and $R^3$ together are trimethylene or triphenylene;
$R^5$ is selected from the group consisting of hydrogen, trifluromethyl and halogen;
$R^6$ is selected from the group consisting of hydrogen, trifluromethyl, halogen and lower alkyl;
X is a leaving group; and
carbon atom denoted as c has the S— or R,S— configuration.

On the other hand, some other preparation methods for preparing imidazo [1,5-a][1,4] diazepine derivatives of following formula(2) were disclosed in U.S. Pat. No. 4,316,839. The compound of formula(2) can be obtained by formylation or dehydrogenation reaction from compound of formula(3), compound of formula(4) and compound of formula(5) which were synthesized by the process disclosed in Belgium Patent Nos. 833,248 and 839,364. However, these preparation method had also some drawbacks due to its long reaction pathway and low yield of end product. The methods can be illustrated as following reaction schemes.

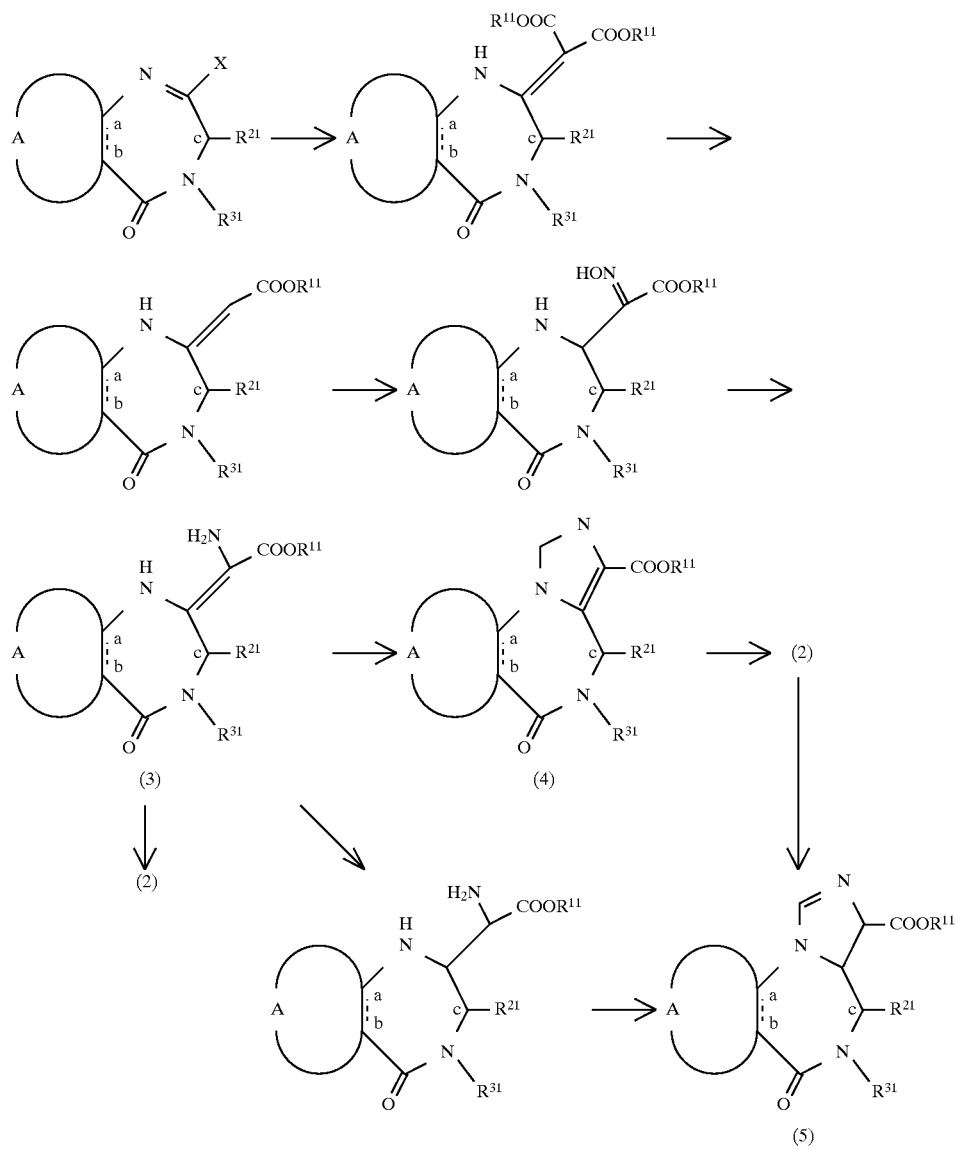

wherein

A and the dotted line represents the same as above;

$R^{11}$, $R^{21}$ and $R^{31}$ represents the same as $R^1$, $R^2$, and $R^3$ described above respectively; and X is a leaving group.

(SUMMARY OF THE INVENTION)

The object of the present invention is to provide an improved process for preparing benzodiazepine-3-alkyl carboxylate of formula(I) and its pharmaceutically acceptable salts and esters.

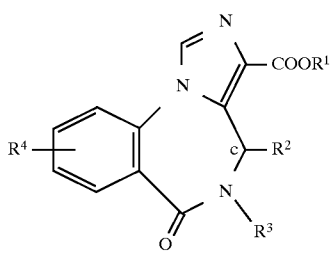

wherein
$R^1$ is methyl, ethyl or isopropyl;
$R^2$ and $R^3$ are each independently hydrogen or $C_1$–$C_6$ lower alkyl;
$R^4$ is hydrogen, halogen or trifluoromethyl;
carbon atom denoted as c has the S— or R, S— configuration.

Furthermore, the intermediate compounds in this invention are novel. Therefore, the present invention provides the novel intermediates in the process therein.

(DETAILED DESCRIPTION OF THE INVENTION)

2-amino benzoic acid derivate of formula(II) is used as starting material.

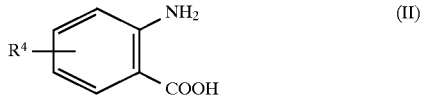

The 2-haloacetamido benzoic acid derivative can be formed by the reaction with compound of formula(II) and haloacetyl halide in the presence of an inert organic solvent, such as, acetonitrile, dimethylsulfoxide, tetrahydrofuran, pyridine or dimethylformamide, preferably, dimethylformamide. 4,1-benzooxazepine-2, 5-dione of formula(III) is obtained in good yield from the reaction mixture by cyclization of 2-haloacetamido benzoic acid derivative in the presence of base, such as, sodiumbicarbonate, potassium carbonate, potassium hydroxide, calcium hydroxide or sodium hydroxide, preferably, sodium hydroxide, which is strongly basic to form the anion of 2-haloacetamido benzoic acid derivative.

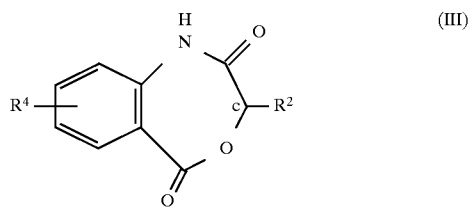

The compound of formula (IV) can be obtained from compound of formula (III) by modifying the known method in U.S. Pat. No. 4,118,386.

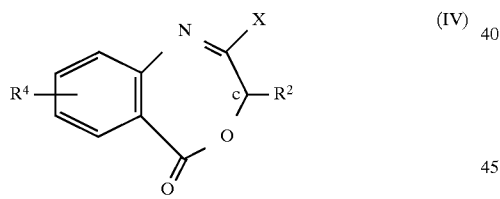

wherein
X is a leaving group, for example, phosphinyl group, halogen atom, alkylthio group aralkyl group, aralkylthio group, n-nitroso alkylamino group or alkoxy group.

The 1,3-double dipole cyclization addition reaction between compound of formula (IV) and isocyano alkyl acetate derivative to form benzooxazepineone of formula (V) is carried out in an inert solvent, for example, dimethylformamide, hexamethylphosphoric acid triamide, dimethyl sulfoxide, tetrahydrofuran or any other suitable inert organic solvent and in the presence of strong base to form the anion of isocyano alkylacetate. Suitable bases are alkali metal alkoxides, such as, sodium methoxide or potassium tert-butoxide; alkali metal hydrides, such as, sodium hydride; alkali metal amides, such as, lithium amide or lithium diisopropylamide; tertiary amines, such as, triethylamine and the like. The reaction is conveniently carried out at a temperature between about –40° C. and about room temperature.

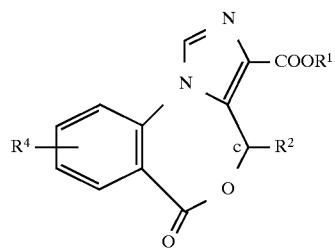

Such benzooxazepineone of formula( V) having imidazole ring is a novel intermediate for preparing benzodiazepine-3-alkyl carboxylate derivatives including flumazenil.

Compound of formula(VI) is obtained by treating compound of formula(V) with lower alkyl amine, such as, methyl amine in the presence of an inert solvent, preferably, dimethylformamide.

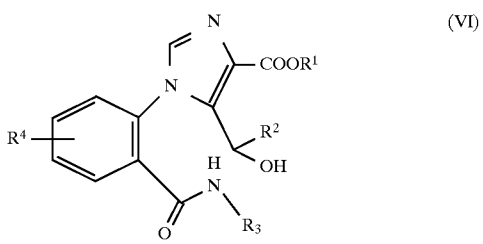

Chloroalkyl compound of formula(VII) is obtained by treating hydroxy alkyl amine compound of formula(VI) with halogenating agents, for example, thionylchloride, phosphorus oxychloride or phosphorustrichloride in the presence of an inert solvent, preferably, dimethylformamide.

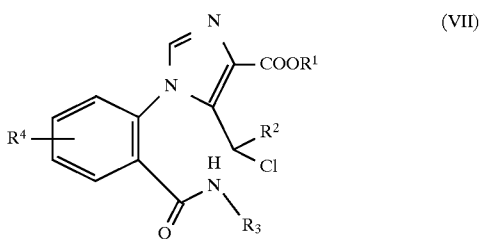

5,6-dihydro-5-methyl-6-oxo-4H-imidazo [1,5-a] [1,4] benzodiazepin3-3-alkyl carboxylate derivative of formula(I) is obtained in good yield by the cyclization of chloroalkyl compound of formula(VII) by the base, for example, alkali metal alkoxides, such as, sodium methoxide or potassium tert-butoxide; alkali metal hydrides, such as, sodium hydride; alkali metal amides, such as, lithium amide or lithium diisopropylamide; tertiary amines, preferably, sodium ethoxide or sodium hydride in the presence of an inert organic solvent, preferably, dimethylformamide. Therefore, it requires two step processes from compound of formula(VI) to compound of formula(I). One of convenient methods is as follows. Compound of formula(VI) is prepared by treating compound of formula(V) with alkylamine in the solution, and halogenating agent is added to form compound of formula(VII). Finally, compound of formula(I) is obtained by cyclization of compound of formula(VII) in the presence of base.

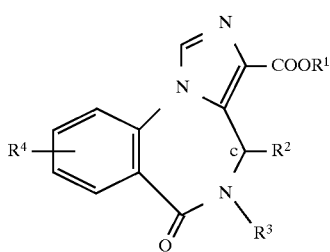

Therefore, flumazenil and its phamacentically acceptable salts and esters are prepared in a convenient preparation method.

The reaction pathway of the present invention can be represented schematically as follows;

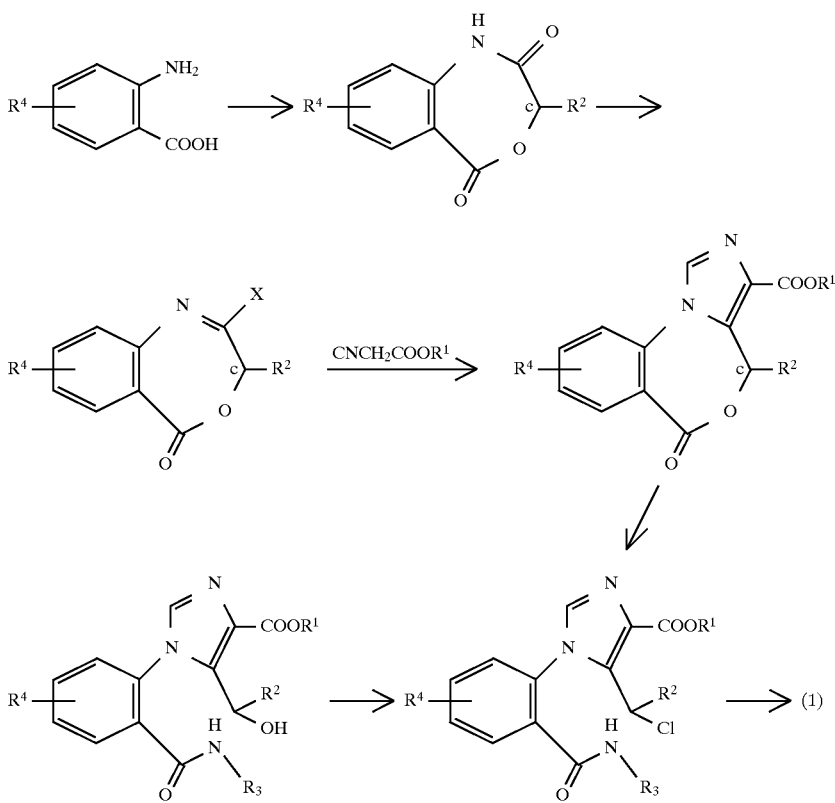

wherein $R^1$ is methyl, ethly, or isopropyl;

$R^2$ and $R^3$ are each independently hydrogen or $C_1$–$C_6$ lower alkyl;

$R^4$ is hydrogen, halogen or trifluoromethyl;

carbon atom denoted as c has the S— or R, S— configuration.

The present invention can be explained in more detail by following examples, but the scope of this invention shall not be construed to be limited by the following examples.

(EXAMPLE 1)

Preparation of 7-fluoro-4,1-benzooxazepine-2,5-(1H, 3H)-dione 2.52 g(13.75 mmol) of bromoacetyl bromide was added for 10 min below 40° C. to the solution having 1.94 g(12.5 mmol) of 2-amino-5-fluorobenzoic acid dissolved in 4 ml of dimethyl formamide. The mixed solution was stirred for 30 min, and the solution having 1.12 g of sodium hydroxide dissolved in 28 ml of water was added. The mixture was slowly heated to 60° C. for 1 hr, then maintained at about 60° C. for 1 hr, and cooled to 5° C. Finally, a crystalline solid of 7-fluoro-4,1-benzooxazepine-2,5-(1H, 3H)-dione of melting point 186° C. was obtained.

$^1$H-NMR(CDCl$_3$):δ10.74(s,1H),7.57~7.51(m,2H),7.23~7.19(m,1H), 4.69(s,2H)
HRMS(FAB):195.9725(M+H$^+$)

(EXAMPLE 2)

Preparation of 3-carboethoxy-5,6-dihydro-8-fluoro-4H-imidazo [1,5-a] [1,4] benzooxazepine-6-one The mixture of 0.585 g(3 mmol) of 7-fluoro-3,4-dihydro-4-methyl-2H-1, 4-benzodiazepine-2,5(1 H)-dione and 8 ml of chloroform with 3.51 ml(27.6 mmol) of dimethylaniline and 0.438 ml(4.5 mmol) of phosphorus oxychloride were refluxed and heated to boil for 1 hr. This mixed solution was poured to the mixture of 1.998 of sodiumbicarbonate and 12 ml of water, and then stirred for 30 min. The mixture was extracted by chloroform, then washed with water, and dried in the presence of magenesium sulfate. After removing the solvent, yellow solution of iminochloride(4.48 g) in the dimethylaniline was obtained. Above obtained iminochloride solution(4.48 g) was added drop by drop to the mixed solution having 3.75 ml of dimethylformamide, 0.627 ml(4.5 mmol) of triethylamine and 0.492 ml(4.5 mmol) of isocyano ethyl acetate in the room temperature. After stirring for one day, the obtained pale brown solution was diluted with water, and then it was extracted by chloroform three times. Above chloroform extract was washed with water, and dried and evaporated in the presence of magnesium sulfate. 0.475 g of 3-carboethoxy-5,6-dihydro-8-fluoro-4H- imidazo [1,5-a] [1,4] benzooxazepine-6-one of melting point 168°~170° C. was obtained by crystallization of residue with ethylacetate(yield:55%)

<sup>1</sup>H-NMR(CDCl<sub>3</sub>):δ7.93(s,1H), 7.80(dd,1H), 7.54~7.43(m, 2H), 5.57(b, 2H), 4.42(q, 2H;J=7.2 Hz), 1.42(t,3H;J=7.2 Hz)

HRMS(FAB):291.0102(M+H<sup>+</sup>)

(EXAMPLE 3)

Preparation of 1-(4-fluoro-2-N-methylcarbamoylphenyl)-2-hydroxymethyl imidazole-3-ethyl carboxylate 0.203 g(0.7 mmol) of 3-carboethoxy-5,6-dihydro-8-fluoro-4H-imidazo [1,5-a] [1,4] benzooxazepine-6-one dissolved in 1 ml of dimethylformamide was treated with 0.40 ml of 30% methylamine methonol solution, and mixed solution was stirred for 1 hr. Water was poured to mixed solution, and the mixed solution was extracted by ethyl acetate. The extract was dried and evaporated in the presence of magenesium sulfate. 0.214 g of 1-(4-fluoro-2-N-methylcarbamoyl-phenyl)-2-hydroxymethyl imidazole-3-ethyl carboxylate of melting point 128°–130 ° C. was obtained by crystallization of residue by ethyl acetate(yield: 95%).

<sup>1</sup>H-NMR(CDCl<sub>3</sub>):δ7.43(s, 1H), 7.40~7.36(m, 1H), 7.25~7.23(m, 2H), 6.74(b, 1H), 5.00(b, 1H), 4.50(b, 1 H), 4.37(q, 2H; J=7.2 Hz), 4.09~4.06(m, 1H), 2.67(d, 3H), 1.39(t, 3H; J=7.2 Hz)

HRMS(FAB):322.0585(M+H<sup>+</sup>)

(EXAMPLE 4)

Preparation of 2-chloromethyl-1-(4-fluoro-2-N-methylcarbamoylphenyl) imidazole-3-ethyl carboxylate 0.161 g(0.5 mmol) of 1-(4-fluoro-2-N-methylcarbamoylphenyl)-2-hydroxy-methyl imidazole-3-ethyl carboxylate dissolved in 1 ml of dimethylformamide was treated with 0.178 g(1.5 mmol) of thionyl chloride, and mixed solution was stirred for 30 min. Water was poured to mixed solution, and the mixed solution was extracted by ethyl acetate. The extract was dried and evaporated in the presence of magenesium sulfate. 0.161 g of 2-chloromethyl-1-(4-fluoro-2-N-methylcarbamoylphenyl) imidazole-3-ethyl carboxylate of melting point 145° C. was obtained by crystallization of residue by ethyl acetate(yield:95%).

<sup>1</sup>H-NMR(CDCl<sub>3</sub>): δ7.53(s, 1H), 7.43~7.24(m, 3H), 5.93(b, 1H), 4.95(s, 2H), 4.40(q, 2H; J=7.2 Hz), 2.74(d, 3H), 1.41(t, 3H; J=7.2 Hz)

HRMS(FAB):340.0107(M+H<sup>+</sup>)

(EXAMPLE 5)

Preparation of 2-chloromethyl-1 - (4-fluoro-2-N-methylcarbamoylphenyl) imidazole-3-ethyl carboxylate from 3-carboethoxy-5,6-dihydro-8-fluoro-4H-imidazo [1,5-a] [1,4] benzooxazepine-6-one 0.203 g(0.7 mmol) of 3-carboethoxy-5,6-dihydro-8-fluoro-4H-imidazo [1,5-a] [1,4] benzooxazepine-6-one dissolved in 1 ml of dimethylformamide was treated with 0.40 ml of 30% methylamine methanol solution, and mixed solution was stirred for 1 hr. After removing excess methylamine, 0.250 g(2.1 mmol) of 1-(4-fluoro-2-N-methylcarbamoyl-phenyl)-2-hydroxymethyl imidazole-3-ethyl carboxylate was treated with 0.250 g(2.1 mmol) of thionyl chloride, and then solution was stirred for 30 min. Water was poured to mixed solution, and the mixed solution was extracted by ethyl acetate. The extract was dried and evaporated in the presence of magenesium sulfate. 0.221 g of 2-chloromethyl-1-(4-fluoro-2-N-methylcarbamoylphenyl) imidazole-3-ethyl carboxylate of melting point 145° C. was obtained by crystallization of residue by ethyl acetate(yield:93%).

<sup>1</sup>H-NMR(CDCl<sub>3</sub>) : δ7.63(s, 1H), 7.72(dd, 1H), 7.43~7.38(m, 1H), 7.34~7.24(m, 1H), 5.20(b, 1 H), 4.39(q, 2H; J=7.2 Hz), 4.27(b, 1H), 3.20(s, 3H), 1.40(t, 3H; J=7.2 Hz)

(EXAMPLE 6)

Preparation of 8-fluoro-5,6-dihydro-5-methyl-6-oxo-4H-imidazo [1,5-a] [1,4] benzodiazepine-3-ethyl carboxylate from 2-chloromethyl-1-(4-fluoro-2-N-methylcarbamoylphenyl) imidazole-3-ethyl carboxylate The mixture of 0.340 g(1 mmol) of 2-chloromethyl-1-(4-fluoro-2-N-methyl-carbamoylphenyl) imidazole-3-ethyl carboxylate and 3 ml of ethanol were refluxed and heated to boil for 30 min with 0.075 g(1.1 mmol) of sodium ethoxide. Water was poured to mixed solution, and the mixed solution was extracted by ethyl acetate. The extract was dried and evaporated in the presence of magenesium sulfate. 0.294 g of 8-fluoro-5,6-dihydro-5-methyl-6-oxo-4H-imidazo [1,5-a] [1,4] benzodiazepine-3-ethyl carboxylate of melting point 201°~203° C. was obtained by crystallization of residue by ethyl acetate(yield 97%).

We claim:

1. A process for preparing a compound of formula(I) and its pharmaceutically acceptable salts

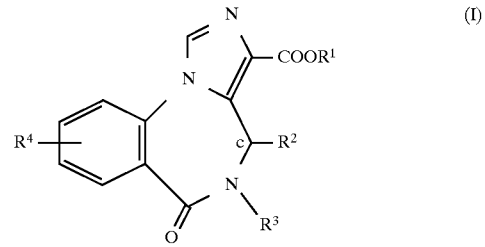

wherein $R^1$ is methyl, ethyl or isopropyl;

$R^2$ and $R^3$ are each independently hydrogen or $C_1$–$C_6$ lower alkyl;

$R^4$ is hydrogen, halogen or trifluoromethyl;

carbon atom denoted as c has the S— or R, S— configuration;

comprising the steps of:
i) preparing the compound of formula(VI) by treating compound of formula (V) with lower alkyl amine in an inert organic solvent;

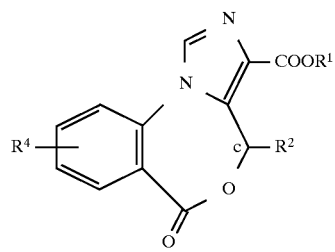 (V)

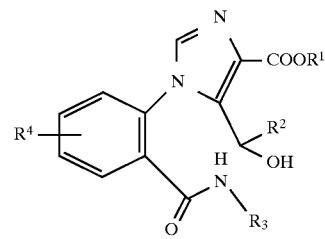 (VI)

ii) preparing the compound of formula(VII) by addition of halogenating agent to compound of formula(VI); and

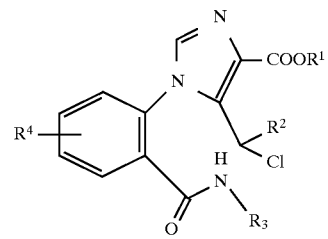 (VI)

iii) cyclization of compound of formula(VII) in the presence of base to form the compound of formula (I).

2. The process for preparing compound of formula(I) and its pharmaceutically acceptable salts and esters according to claim 1, wherein the compound of formula(V) is prepared with the steps comprising:

i) preparing the compound of formula(III) by cyclization of compound of formula(II) with haloacetyl halide in the presence of base;

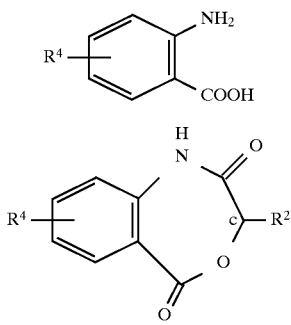

(II)

(III)

ii) preparing the compound of formula(IV) by addition of leaving group(X) to compound of formula(III); and

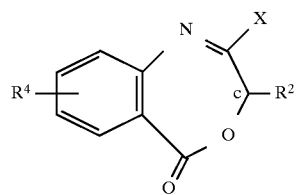 (IV)

wherein

X is a leaving group, phosphinyl group, halogen atom, alkylthio group, aralkyl group, aralkylthio group, n-nitroso alkylamino group or alkoxy group, iii) preparing compound of formula(V) by reacting isocyano alkyl acetate in the presence of strong base and inert organic solvent.

3. The process for preparing the compound of formula(I) and its pharmaceutically acceptable salts according to claim 1, wherein the base is selected from the group consisting of alkali metal alkoxides, alkali metal hydrides, alkali metal amides and tertiary amines.

4. The process for preparing the compound of formula(I) and its pharmaceutically acceptable salts according to claim 2, wherein the base is selected from the group consisting of alkali metal alkoxides, alkali metal hydrides, alkali metal amides and tertiary amines.

5. The process for preparing the compound of formula(I) and its pharmaceutically acceptable salts according to claim 1, wherein the inert solvent is selected from the group consisting of dimethylformamide, hexamethylphosphoric acid triamide, dimethyl sulfoxide and tetrahydrofuran.

6. The process for preparing the compound of formula(I) and its pharmaceutically acceptable salts according to claim 2, wherein the inert solvent is selected from the group consisting of dimethylformamide, hexamethylphosphoric acid triamide, dimethyl sulfoxide and tetrahydrofuran.

7. An intermediate compound of formula(V) for preparing the compound of formula(I) and its pharmaceutically acceptable salts

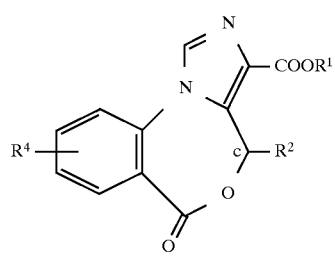 (V)

wherein $R^1$ is methyl, ethyl or isopropyl;

$R^2$ is hydrogen or $C_1$–$C_6$ lower alkyl;

$R^4$ is hydrogen, halogen or trifluoromethyl;

carbon atom denoted as c has the S— or R, S— configuration.

* * * * *

UNITED STATES PATENT AND TRADEMARK OFFICE
CERTIFICATE OF CORRECTION

PATENT NO. : 5,817,808
DATED : 6 October 1998
INVENTOR(S) : Yong Hae KIM et al.

It is certified that error appears in the above-identified patent and that said Letters Patent is hereby corrected as shown below:

| Column | Line | |
|--------|------|---|
| 2 | 46 | Change "trifluromethyl" to --trifluoromethyl--. |
| 2 | 48 | Change "trifluromethyl" to --trifluoromethyl--. |
| 5 | 18 | Change "4,1-benzooxazepine-2, 5-dione" to --4,1-benzooxazepine-2,5-dione--. |
| 5 | 50 | After "alkylthio group" insert --,--. |
| 12 | 11 | After "leaving group" insert --selected from the group consisting of --. |
| 12 | 13 | After "alkoxy group" change "," to --;--. |

Signed and Sealed this

Eighteenth Day of May, 1999

Attest:

Q. TODD DICKINSON

*Attesting Officer*   Acting Commissioner of Patents and Trademarks